United States Patent [19]

Van der Salm

[11] Patent Number: Plant 6,528

[45] Date of Patent: Jan. 10, 1989

[54] LILY PLANT NAMED 'CHERISHED'

[76] Inventor: Geradus C. Van der Salm, Rte. 1, Box 422, Woodland, Wash. 98674

[21] Appl. No.: 25,829

[22] Filed: Mar. 13, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Klarquist, Sparkman, Campbell, Leigh & Whinston

[57] ABSTRACT

A new variety of hybrid lily plant bearing large clusters of flowers of excellent form and long persistence, both on the plant and as cut-flowers. The flowers of the new plant are particularly characterized by their clear pink coloration shading into a cream "blush" above the nectaries, by their dainty "ring" of spots in the center of the flowers only, and by their deeper pink tepal reverse. This combination is completely new in the upright Asiatic divisions of lilies suited to forcing and to mass commercial cultivation. The plant is highly resistant to disease and shows high tolerance of virus. It is an excellent garden plant. The bulbs may be precooled and forced for cut-flower production. The new lily plant is vigorous and is a good grower and propagator.

1 Drawing Sheet

BACKGROUND AND SUMMARY OF THE INVENTION

This invention relates to a new and distinct variety of lily classified botanically as a lilium hybrid and commercially as an upright Asiatic hybrid. I have selected the name "Cherished" as the varietal name for my plant.

My new variety of lily plant originated as a seedling selected from a group of seedlings at Julianadorp, The Netherlands. The seedlings were planted as a result of breeding efforts carried on by me since 1976. The breeding efforts had as their objective the production of upright Asiatic lilies in shades of pink and rose, well suited to forcing for cut-flower production out of season, heretofore unknown in the lily breeding art.

I achieved the desired objective by extensive interpollinations among many hybrid lily cultivars.

The flowers of my new lily are characterized by an upright orientation; by a dainty "ring" of spots, confined to the center of the flowers; and by their distinctive clear pink color shading into a cream "blush" above the nectaries, contrasting with their deeper pink tepal reverse, a color pattern unique in this type of lily. p In addition, my new lily plant possesses to a high degree desirable characteristics of hybrid vigor, great hardiness, and disease resistance, including a high tolerance of virus. It possesses all of the desired characteristics of excellence of form, color and habit. Its excellently formed flowers, of large size, are produced on a single stalk. The new lily plant is vigorous, a good grower, and a rapid propagator, as observed at Julianadorp, The Netherlands, and at Woodland, Wash.

Also, my new lily plant has versatility both as a garden plant and as a cut flower producer. It is well suited to forcing out of season when the bulbs are dug at the appropriate time and properly precooled October-dug bulbs, properly precooled and potted in January, will flower under glass in Western Oregon, with no supplementary lighting and at moderate greenhouse temperatures, in an average of seventy to eighty days.

My new variety of Asiatic hybrid lily most nearly resembles the lily "Corsica," which is the subject of U.S. Plant patent application, Ser. No. 902,461, filed Aug. 29, 1986, but it has a clear pink coloration suffusing gradually into a small "blush" of cream, rather than the sharply defined white/pink bicolored pattern of "Corsica." The cream "blush" of my new lily is initially a soft yellow-gold, in contrast with the white center of the "Corsica" lily. Also, the flowers of my new lily carry a distinctive 10–15 mm wide "ring" of small, deep-colored spots, in contrast with the less conspicuous spotting of the flowers of the "Corsica" lily. Also, my new lily has longer pedicels, a smaller stigma, and a somewhat deeper stem color than does the "Corsica" lily.

My new variety of lily plant has been asexually reproduced by me and under my direction at Julianadorp, The Netherlands and at Woodland, Wash. Successive generations produced by bulb scale propagation and by natural propagation from bulblets have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing, which shows the open bloom in full color and illustrates the flower form, the tepal arrangement, the connection of the flower to the stem, and in particular the novel and distinctive clear pink flowers with a "blush" of cream above the nectaries, and accented with a dainty "ring" of spots in the flower's center only.

DETAILED DESCRIPTION OF MY NEW VARIETY

The following is a detailed description of my new variety of Asiatic hybrid lily, with nomenclature according to the *International Lily Register* (Royal Horticultural Society of London, Second Edition, 1969), and with color designations according to the Colour Chart of The Royal Horticultural Society, published by the Society in 1966.

THE PLANT

Origin: Seedling.

Seed parent: Unnamed seedling. Pollen parent: Unnamed seedling.

Commercial classification: Hybrid Lilium clone.

Horticultural classification: Division I-A, upright Asiatic hybrid lily, according to the Horticultural Classification of Lilies, Royal Horticultural Society of London.

Form: Single stem, erect and stately.

Height: 70–100 cm from bulbs 15 to 18 cm in circumference, provided their light levels are adequate; low light levels may cause "stretching."

Growth: Vigorous and upright.

Foliage quantity: Abundant.

Size of leaf: 8 to 12 cam long by 5 to 12 mm wide; leaves are longer near the top of the stem and shorter at its base.

Shape of leaf: Lanceolate (pointed).

Texture: Leathery and glossy; apex of leaves may be lightly pubescent.

Color: Dark green, lighter on lower side.

Bulb size: Any size, ranging to 25 cm circumference commercially.

Bulb color: White.

The Bud

Form: Obtuse, ovoid and long.

Size: 8 to 9 cm long and 7 cm in circumference just prior to opening.

Opening: Bud opens slowly, in response to morning light; this takes about one hour.

Color: RHS CC Red-purple 59 C overlaid with light green along the midribs, just prior to bud's opening. The tepal reverse retains its deep rose color after the bud opens.

Peduncle: Averages 4 to 6 cm, but it may elongate if light levels are too low or if bulbs have been improperly stored prior to forcing. Color is dark green with plum overlay.

The Flower

Blooming habit: Annually in midseason; flowers once and profusely.

Size: Flowers are large-sized for Asiatic hybrids. They average 14 to 17 cm in diameter; the outer tepals average 2 to 2.5 cm wide, and the inner tepals average 3 cm wide.

Borne: In a single racemic inflorescence producing 7 to 12 buds (from a bulb 18 cm in circumference)

Shape: First open in cup shape, which flattens as tepals recurve by their second day.

Tepalage: Typical of genus Lilium, with 6 imbricated tepals.

Tepal color: Flowers are distinguished by their clear pink tepals with a cream "blush" above the nectaries. The base color of the tepal is RHS CC red-purple 63 D, which gradually deepens to RHS CC 63 B-C along the tepals margins and in a 2–3 mm band along the tepal midrib. The center of the flower is a deeper pink; the area parallel to the nectaries is RHS CC red 51B-C. A "blush" of RHS CC yellow-orange 18 D to RHS CC yellow 11 D, 10–20 mm wide and 20 to 40 mm long, extends along the center of the tepals from the nectaries outward. This cream portion of the tepal is more noticeable on the outer tepals, where a smaller part of it is overlaid with pink pigment than is "covered" on the inner tepals. The pink color is affected by temperature and light levels; it decreases with very high temperatures and with low light levels. The nectary furrows are lightly pubescent and are soft pink, RHS CC 62 D.

Tepal spotting: There is a dainty "ring" formed by tiny deep magenta spots at the basal 10–15 mm of each tepal.

Tepal longevity: Tepals stay on stems about three weeks.

Pedicel length: Average 6 to 12 cm long.

Pedicel color: Deep green with plum overlay.

Pedicel form: Sturdy and ascending up to 45 degrees from the horizontal. Occasional secondary buds.

Color changes: As the flowers age, they may become slightly lighter and a more lavender-toned pink, approaching RHS CC 68 D with RHS CC 68 B-C tips and "ray" along the tepal midrib. Low light levels and extreme heat may cause the pink pigmentation to decrease; changes will be inconspicuous if light levels are adequate for cut-flower maintenance.

Appearance: Flower is shiny.

Disease resistance: The flower and plant are resistant to disease; in particular, they are resistant to Fusarium bulb rot and Botrutis blight.

Fragrance: None.

Lasting quality: The flower is long lasting, both on the plant and as a cut-flower.

The Reproductive Organs

Stamens and anthers: Arrangement typical of genus Lilium. Six stamens with soft pink (RHS CC greyed purple 184 D) filaments 5 cm long.

Pollen and anthers (dehisced): RHS CC greyed red 178 A, but it is not copious; the dehisced anther shows some of the underlying tapetal tissue and gives the visual appearance of RHS CC greyed-purple 187 A.

Pistil: One in number, 5 cm long.

Stigma: Soft cream to very light pink, medium in size.

Characteristics of ovary: Characteristic of genus Lilium.

The Fruit

Fertility: The fruit is fertile.

Shape: Ovoid.

Color at maturity: Soft brown, sometimes overlaid with soft plum.

I claim:

1. A new and distinctive variety of Asiatic hybrid lily plant substantially as herein shown and described.

* * * * *

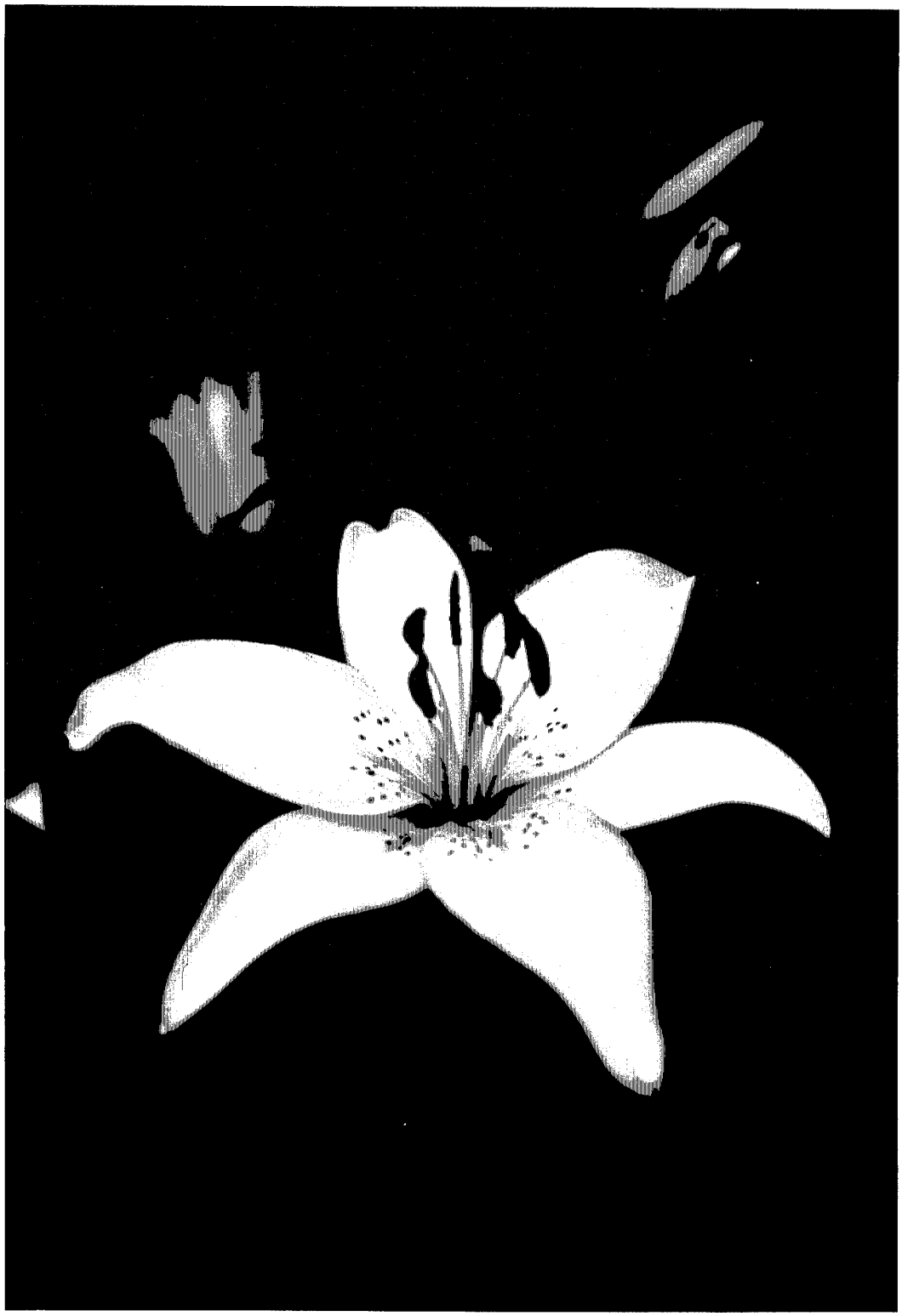

UNITED STATES PATENT AND TRADEMARK OFFICE

CERTIFICATE OF CORRECTION

PATENT NO. : Plant 6,528

DATED : January 10, 1989

INVENTOR(S) : Gerardus C. Van der Salm

It is certified that error appears in the above-identified patent and that said Letters Patent is hereby corrected as shown below:

In the Heading:

Item [76] for Inventor: Inventor's name should read "Gerardus", not "Geradus".

Column 1, line 24, delete the "p" before the word "In".

Column 3, line 12, "cam" should be "cm".

Signed and Sealed this

Twelfth Day of December, 1989

*Attest:*

JEFFREY M. SAMUELS

*Attesting Officer* *Acting Commissioner of Patents and Trademarks*